United States Patent
Atkinson et al.

(10) Patent No.: US 6,752,182 B2
(45) Date of Patent: Jun. 22, 2004

(54) MICROARRAYING APPARATUS, PIN HEAD THEREFOR AND SPOTTING METHOD

(75) Inventors: George Robert Atkinson, Walkford (GB); James Keith Haslam, Shapwick Blandford Forum (GB)

(73) Assignee: Genetix Limited, Hampshire (GB)

( * ) Notice: Subject to any disclaimer, the term of this patent is extended or adjusted under 35 U.S.C. 154(b) by 173 days.

(21) Appl. No.: 09/892,614

(22) Filed: Jun. 28, 2001

(65) Prior Publication Data

US 2003/0002962 A1 Jan. 2, 2003

(51) Int. Cl.$^7$ ................................................. B65B 1/04
(52) U.S. Cl. .................. 141/130; 422/99; 422/100; 382/133; 73/863.01
(58) Field of Search ....................... 422/99, 100, 105, 422/63, 68.1; 141/130; 382/133, 134; 356/614, 237.1, 237.6; 73/863.01, 864.01, 864.11, 864.25

(56) References Cited

U.S. PATENT DOCUMENTS 6,269,846 B1 * 8/2001 Overbeck et al. .............. 141/1
6,447,723 B1 * 9/2002 Schermer et al. ............. 422/62
6,454,924 B2 * 9/2002 Jedrzejewski et al. ...... 204/601
6,558,623 B1 * 5/2003 Ganz et al. ................... 422/63

* cited by examiner

Primary Examiner—Steven O. Douglas
(74) Attorney, Agent, or Firm—Foley & Lardner

(57) ABSTRACT

The invention is based on the realization that feedback control for the vertical drive of a pin head becomes unnecessary if one instead prealigns the relative heights of the spotting surface and the well plates such that the pins in the pin head are lowered to the same absolute height both for picking up liquid from the well plates and depositing it onto the spotting surface. By aligning the heights of the well plates and spotting surfaces, the vertical drive of the pin head needs only to be able to reproducibly and accurately arrive at a single lowered position. A pin head can provide this functionality by having a mechanically defined bottom point, obviating the need for a complex and costly feedback control system for height determination of the pins. A simple, low-cost micro-arrayer can thus be provided.

14 Claims, 6 Drawing Sheets

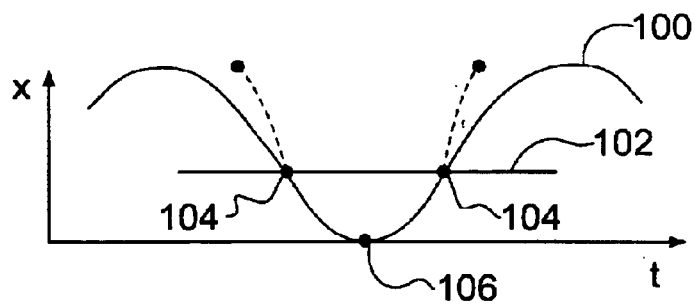
Fig. 5
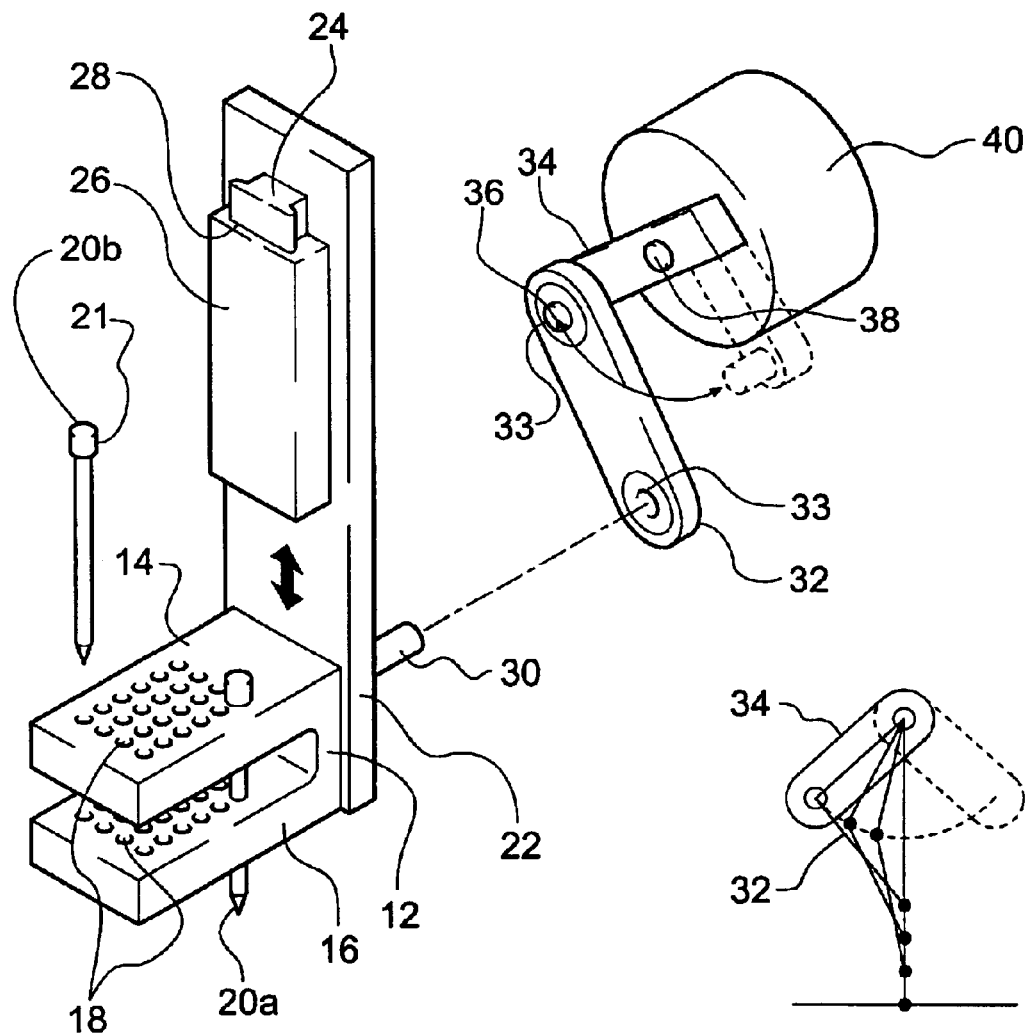
Fig. 1
Fig. 4

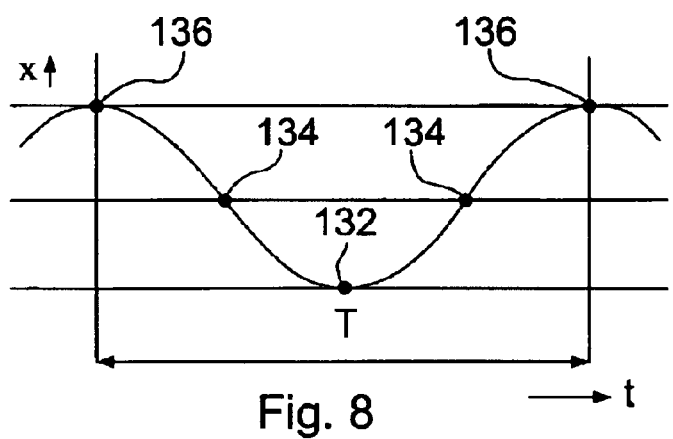
Fig. 8
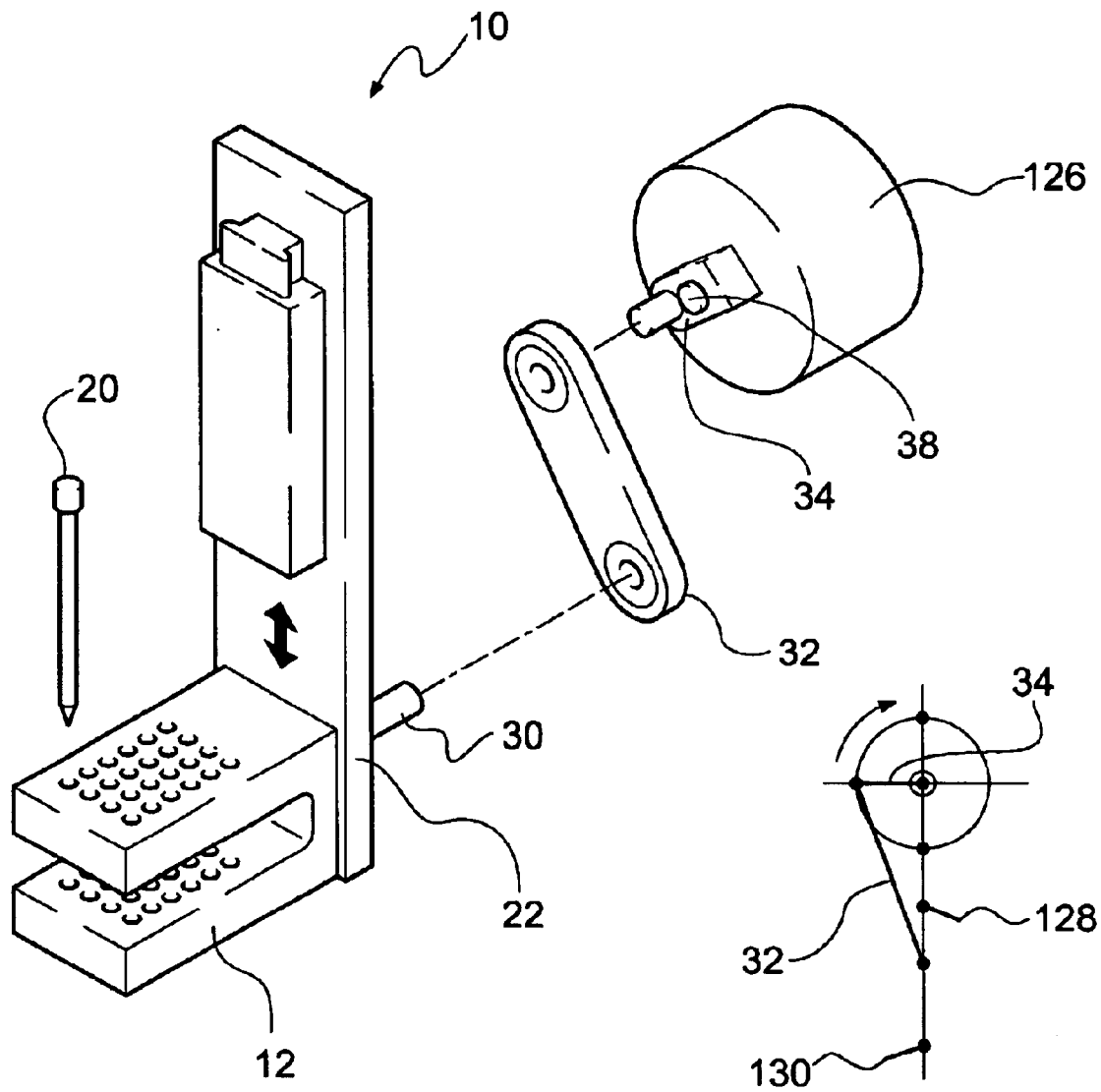
Fig. 6
Fig. 7

MICROARRAYING APPARATUS, PIN HEAD THEREFOR AND SPOTTING METHOD

BACKGROUND OF THE INVENTION

The invention relates to microarraying and spotting, more especially but not exclusively to microarraying apparatus and to pin heads for microarraying apparatus.

Microarraying is a technique in widespread use in fields such as chemistry and biotechnology. Liquid samples are stored in the wells of a well plate. The liquid may be assays or any other biological or chemical sample of interest. To spot the liquid from a well, a pin is dipped in the well to retrieve an amount of the liquid. The pin carrying an amount of the liquid is then moved across to a spotting surface of a microscope slide or other suitable surface. A spot of liquid is deposited on the slide by bringing the pin into close proximity with the slide surface, or by physically contacting the tip of the pin with the slide surface.

In general, a plurality of slides and well plates are arranged on a surface of a microarraying apparatus. An array of pins is held in a pin holder which is mounted on a frame above the arraying surface. A motorized positioning system is provided to move the pin holder laterally about the frame so that the pins can be moved between the slides and well plates, and other areas such as a wash station. A vertical positioner or drive is also provided for causing vertical motion of the pins. This allows the pins to be dipped into the well plates and also allows the pins to be brought into contact with the slides for spotting.

Typically, microarraying apparatus of this type are large and costly pieces of equipment intended for large scale use, and are capable of handling a large volume of well plates and slides. Given the repetitive nature of the spotting procedure and the large lateral distances between the well plates and spotting surfaces of the slides, the vertical pin drive is required to have the capability of returning exactly to any desired absolute height position many thousands or tens of thousands of times without any long term drift.

For example, the pin drive must be able to dip the pins into the wells to a suitable depth to pick up liquid, and also to deposit the liquid as desired on a spotting surface. Spotting requires that the pin or pins approach the spotting surface with great precision, in order to be close enough for effective deposit of the liquid without the pin crashing into the slide. In other words, attaining an appropriate clearance height during spotting is critical, and must take account of factors such as use of slides of different thicknesses. Similarly, well plates may be of different thicknesses or have reservoirs filled to different levels.

To attain the necessary specification, the pin drive is typically provided with some kind of height sensing with feedback, such as an interferometric encoder system. Although precision feedback systems for accurate height sensing are effective and available with established technology, they are costly, and contribute substantially to the overall cost of a microarraying apparatus.

While cost is not a major factor for high volume applications, it is a considerable deterrent to the more widespread use of microarraying for smaller scale research projects.

SUMMARY OF THE INVENTION

The invention is based on the realization that feedback control for the pin drive becomes unnecessary if one instead prealigns the relative heights of the spotting surface and the well plates such that the pins in the pin head can be lowered to the same absolute height both for picking up liquid from the well plates and depositing it onto the spotting surface. By aligning the heights of the well plates relative to the spotting surfaces, the pin drive needs only to be able to reproducibly and accurately arrive at a single lowered position. Building from this realization, it has been further appreciated that a pin head can be designed to achieve this functionality purely with a mechanically defined bottom point, obviating the need for an encoder or other feedback control system for height determination of the pins. Moreover, it is a simple matter to provide a height adjustable platform for supporting the area carrying the well plates, or alternatively a height adjustable platform for supporting the area carrying the microscope slides for spotting onto. Through these measures it becomes possible to produce a microarraying apparatus of significantly reduced cost that can be used for small-scale experimentation.

Accordingly, a first aspect of the invention is directed to a pin head for a microarraying apparatus comprising: a pin holder for carrying an array of pins; a vertical drive operable to move the pin holder in a vertical axis; and a positioning mechanism that cooperates with the vertical drive to mechanically define a lowest point of travel for the pins in the vertical axis.

Moreover, a second aspect of the invention is directed to a microarraying apparatus comprising: an apparatus bed defining an arraying surface for carrying one or more slides; a well plate platform for carrying at least one well plate; and a height adjustment mechanism operable to alter the height of the well plate platform relative to that of the apparatus bed.

In use, the microarraying apparatus is aligned before use using the height adjustment mechanism, which is preferably manually actuatable for simplicity and cost reasons. Alignment is achieved by ensuring that the horizontal plane defined by the lowest point of travel of the pins lies an appropriate distance below the surface of the liquid held in the well plates and an appropriate distance above the spotting surface of the slides (which may be zero in the case of near-contact of the pin tips with the spotting surface).

The pin holder has simple vertical motion with a defined lowest position in which the pin holder can be readily located without the need for complex encoder systems. This arrangement permits a microarraying apparatus to be set up with its component parts positioned correctly with respect to the position of the pins when the pin holder is in the lowest position, so that spotting can be carried out without the need for control of the vertical position of the pins during the spotting process.

For some applications where pins are individually fired to the bottom position, the vertical drive may be connected directly to the pins rather than via the pin holder in which case there may be provided a pin head for a microarraying apparatus comprising: a pin holder carrying an array of pins; a vertical drive operable to actuate the pins in a vertical axis individually or collectively; and a positioning mechanism that cooperates with the vertical drive to mechanically define a lowest point of travel of the actuated pins in the vertical axis.

Advantageously, the positioning mechanism comprises a crank system having a bottom dead center and coupled to the pin holder so that the pin holder achieves its lowest position when the crank system is at bottom dead center. A crank system is a simple way of limiting the travel of the pin holder to define the lowest position. Also, the operation of a crank system means that the pin holder and pins therein move at very low velocity and acceleration as the crank system approaches bottom dead center, reaching a momentary static point at the lowest position even if the crank is continuously rotated. This smooth pin approach is highly desirable for ensuring good quality spots are deposited.

The vertical drive may comprise a rotary solenoid or a rotary motor which is coupled to the pin holder by the crank system, the crank system operable to transfer motion produced by the rotary solenoid to the pin holder. A rotary solenoid has the advantage of only requiring a very simple on/off actuation signal. For example, the bottom position may be associated with a deenergized state of the solenoid and a withdrawn position associated with an energized state of the solenoid (or vice versa).

Another aspect of the present invention is directed to a head apparatus combining the above described pin head with an additional height adjustment mechanism. More especially, the head apparatus comprises: a mount adapted to attach a pin head to a microarraying apparatus; a pin head as described above movably mounted on the mount; and a pin head height adjustment arrangement operable to allow the lowest position of the pins to be varied relative to the mount.

A still further aspect of the present invention is directed to a microarraying apparatus comprising: an arraying surface; a slide holder for holding one or more slides mounted on the arraying surface; a well plate platform for holding one or more well plates mounted on the arraying surface; and a platform height adjustment mechanism operable to alter the relative heights of the slide holder and the well plate platform.

The platform height adjuster may be provided with a distance scale which is indicative of the difference in the relative heights of the slide holder and the well plate platform.

The platform height adjuster facilitates setting up the apparatus so that the slides and well plates are at heights at which dipping and spotting can be performed with the same lowest vertical pin position.

It will be appreciated that further height adjustable platforms may be provided, for example for a wash station, so that pins are dipped into cleansing liquid in the wash station to a sufficient depth for cleaning.

The microarraying apparatus may further comprise a mounting frame mounted over the arraying surface; and a pin head mounted on the mounting frame. The pin head is provided with a drive system operable to move the pin head in a plane parallel to the arraying surface. The pin head comprises a pin holder for holding an array of pins, a vertical drive operable to move the pin holder along a vertical axis, and a positioning mechanism which defines a furthest point of travel of the pin holder along the vertical axis, the furthest point being the lowest position achievable by the pin holder.

In this way, a simple pin head which has a repeatable lowest position can be used for dipping and spotting. Specifically, precision, accuracy and reproducibility are achievable without the need for a feed-back-controlled pin head, since the pin head is only required to be able to find its bottom position precisely, accurately and reproducibly, which can be performed with a variety of simple mechanical or electromechanical solutions.

A still further aspect of the invention is directed to a spotting method using a microarrayer having an apparatus bed and a well plate platform, the method comprising:

arranging at least one slide on the apparatus bed to provide a spotting surface;

arranging a well plate filled to a level with spotting liquid on the well plate platform;

vertically aligning the well plate platform relative to the apparatus bed so that the spotting surface lies at a desired height at or below the level of the spotting liquid;

dipping a pin from a pin head into the spotting liquid by moving the pin to a lowered position;

moving the pin head across the microarrayer to a spotting position; and depositing the spotting liquid onto the spotting surface by moving the pin once again to the lowered position.

BRIEF DESCRIPTION OF THE DRAWINGS

For a better understanding of the invention and to show how the same may be carried into effect reference is now made by way of example to the accompanying drawings in which:

FIG. 1 shows a partially exploded perspective view of a first embodiment of a pin head employing a crank system and a rotary solenoid;

FIG. 4 shows a schematic diagram of the crank system of FIG. 1;

FIG. 5 shows a graph of the variation of the vertical position of a pin holder comprising part of the pin head of FIG. 1;

FIG. 6 shows a partially exploded perspective view of a pin head according to a second embodiment also having a crank and based on an electric motor;

FIG. 7 shows a schematic diagram of the crank system of FIG. 6;

FIG. 8 shows a graph of the variation of the vertical position of a pin holder comprising part of the pin head of FIG. 6;

DETAILED DESCRIPTION

First Embodiment of Pin Head

Figure 2:
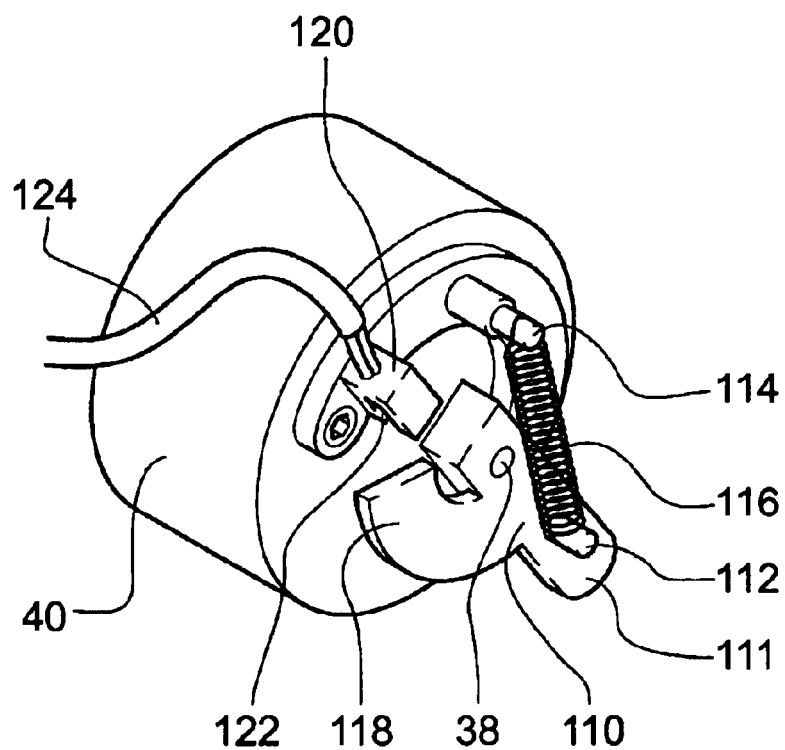
FIG. 2 shows a perspective rear view of the rotary solenoid of FIG. 1.

FIG. 1 shows a partially exploded view of an embodiment of a pin head.

The pin head 10 has a pin holder 12, which comprises an upper plate 14 and a lower plate 16. The plates 14, 16 each have a matrix of holes 18, the holes 18 in the upper plate 14 being positioned vertically above the holes 18 in the lower plates 16. The holes 18 receive pins 20. Each pin 20 has a head 21 of a larger diameter than the holes 18. A pin 20 passes through a hole in the upper plate 14 and through the correspondingly positioned hole 18 in the lower plate 16. The head 21 of the pin 20 prevents the pin from passing completely through the hole 18 in the upper plate 14 so that the pin 20 is hangs freely in position in the pin holder. For the sake of clarity, FIG. 1 shows one pin 20a in position in the pin holder, and one pin 20b about to be inserted into the pin holder 12. In use, each pair of holes 18 in the upper and lower plates 14, 16 will hold a pin 20. The pin holder 12 in FIG. 1 holds twenty-four pins 20 in a six by four array, but other quantities of pins 20 may be accommodated, for example forty-eight.

This pin head arrangement is but one of a variety of possible arrangements. It will be understood that the manner in which the pins are accommodated in the pin head is not relevant for implementing the invention, so that a variety of pin housing schemes may be used, as will be familiar to a person skilled in the art.

The pin holder 12 is affixed to one side of an elongate vertical member 22, towards the lower end of the vertical member. The same side of the upper end of the vertical member 22 has an elongate protrusion 24 positioned longitudinally along it. The protrusion 24 is substantially T-shaped in cross-section. An attachment member 26 has an elongate recess 28 also of substantially T-shape cross-section. The recess 28 receives the protrusion 24 which can slide freely within it. Thus the recess 28 and the protrusion 24 together form a linear bearing which allows the vertical member 22, and the pin holder 12 mounted thereon, to slide vertically with respect to the attachment member 26.

At the lower end of the vertical member 22, on the reverse side to the pin holder 12, there is a first peg 30, for the purpose of coupling the pin holder to a vertical drive. The coupling is achieved by means of a crank system, comprising a first crank shaft 32 which is elongate and has a hole 33 at each end, and a second crank shaft 34 which is also elongate, and has a second peg 36 at one end. The first crank shaft 32 joins the vertical member 22 to the second crank shaft 34 by means of its two holes 33, one of which receives the first peg 30 and the other of which receives the second peg 36. The pegs 30, 36 can rotate freely in the holes 33. The end of the second crank shaft 34 distal from the second peg 36 is coupled to a rotary solenoid 40 by means of an axle 38. The rotary solenoid is connected to a source of reversible current (not shown), and comprises the vertical drive of the pin head.

In use, the pin head 10 is fixed to a microarraying apparatus by means of the attachment member 26, so that the attachment member is fixed in relation to the microarraying apparatus. Therefore, the vertical member 22 and pin holder 12 are free to slide vertically in relation to the microarraying apparatus by means of the linear bearing formed by the protrusion 24 and the recess 26.

The vertical motion of the pin holder 12 is controlled by the rotary solenoid 40. Application of current to the rotary solenoid 40 causes the second crank shaft 34 to rotate first in one direction, to the position shown by the solid lines in FIG. 1, owing to magnetization of the solenoid in the conventional fashion. Reversal of the current causes rotation in the opposite direction, to the position indicated by the broken lines in FIG. 1. The second crank shaft 34 is preferably constrained so that rotation from one extreme to the other covers 110°, although other angles of rotation can be used as appropriate.

The movement of the second crank shaft 34 is transferred via the first crank shaft 32 to the vertical member 22, which is moved up and down within the linear bearing as the second crank shaft 34 rotates from side to side. The vertical member 22, and hence the pin holder 12, reach an uppermost position when the second crank shaft 34 is at either of the two extremes of rotation. The vertical member 22 and pin holder 12 reach a lowest position when the second crank shaft 34 is positioned vertically, midway between the two extremes of rotation. This is at the bottom dead center of the crank system, at which point the two crank shafts are extended to their fullest reach so that this is the furthest travel which the pin holder can achieve. The pins therefore reach the lowest position once per reversal of the alternating current, so that there is a defined pin position which is repeatedly achievable without the need for computer control or the like. In this way, the crank system acts as a positioning mechanism which defines the lowest vertical position which the pin holder, and hence the pins, can reach. This contrasts with pin holders controlled by encoded motorized drive systems in which encoded feedback control of the motor is required to locate the pins at any predetermined position.

When the current is removed from the rotary solenoid 40, the solenoid 40 is demagnetized and no longer acts on the second crank shaft 34. Therefore, the crank system falls freely under its own weight (and the weight of the pin head to which it is coupled) to the bottom dead center position. Hence, the pin holder falls to its lowest position.

This behavior means that the pin holder 12 always returns to the lowest position when no current is applied to the rotary solenoid 40. Therefore, the pin holder 12, and the pins 20 held therein revert to the defined lowest position, which can be repeatedly and consistently achieved merely by removing the current. This permits microarraying apparatus to be set up easily with respect to this defined lower pin position.

However, in some instances it may be desirable for the pin holder 12 and pins 20 to be retained in an upper position when not in use, while still being consistently locatable in the lower position. This affords protection to the pins, as they can be "stored" in an upper position, possibly within a housing or casing, which protects them from accidental damage.

FIG. 2 shows a perspective rear view of a rotary solenoid suitable for this purpose. The solenoid 40 has a lever 110 connected at one end to the axle 38 of the solenoid 40. The lever 110 has a first post 112 protruding from its distal end. The distal end terminates in a handle portion 111 which extends beyond the edge of the solenoid 40. A second post 114 protrudes from the rear of the solenoid 40, positioned above the axle 38 and in line with the bottom dead center of the crank system. A coil spring 116 extends between the two posts 112, 114.

The lever 110 has a sensor shutter 118 extending from its side, and having the form of a flat protrusion. A sensor gate 120 is located on the rear surface of the solenoid 40, having an opening 122 which can receive the shutter 118. An optical source (not shown) such as a light emitting diode (LED), and an optical detector (not shown), are located within the gate 120, one on each side of the opening. Together these components form an optical position sensor. Cabling 124 carries power to the optical source and response signals from the optical detector. The power can be provided from the power source which drives the solenoid 40. The response signals are passed to the solenoid power source, which is adapted to respond to the signals.

In use, a pulse of current is applied to energize the solenoid 40, which moves the crank system in the manner previously described. The lever 110 is rotated with the second crank shaft 34 via its attachment to the axle 38. The pulse is applied for a time sufficient to carry the crank system, and hence the lever 110, from one extreme of rotation over roughly a third of second crank shaft's permitted travel. Once the pulse ceases, the solenoid 40 is de-energized, but the crank system and the lever 110 continue to travel, carried by inertia, over a further third of the permitted travel. The crank system therefore coasts through its bottom dead center, and the pins pass through their lowest position.

Following this, the spring 114, which has been stretched by the lever passing the bottom dead center position, is able to contract and hence pulls the lever further round, carrying the crank system with it round to the other extreme of rotation. Braking can be achieved by shorting the solenoid coils which provides a back e.m.f., thus ensuring that the crank system is brought to a smooth halt.

In this manner, the spring carries the pins and pin holder to an upper position, corresponding to an extreme of rotation of the crank system, when the solenoid is demagnetized. Thus the pins can be protected when not in use. The device is therefore mechanically bi-stable, as it returns to one or other of the extreme positions when not in use. When the solenoid is demagnetized, with the pins in an upper position, the pins can be moved in their lowest position by means of the lever 110. The lowest position is, however, unstable. The lever can be manually toggled back and forth against the force of the spring 116. When the crank system is located at bottom dead center, the spring 116 is balanced and does not pull the lever 110 to either side.

Figure 3:
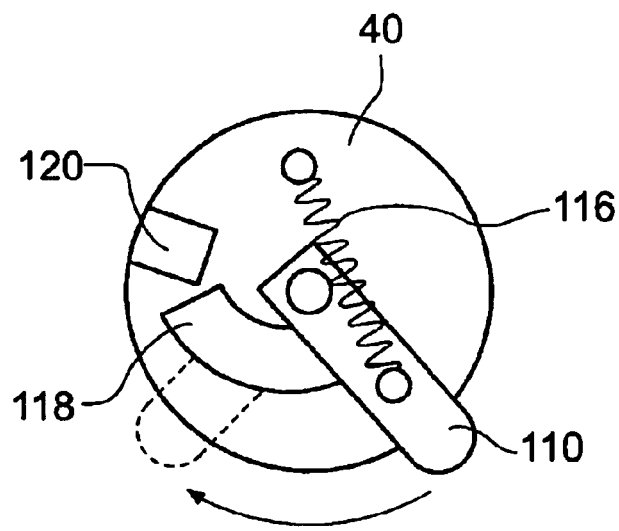
FIG. 3 shows a plan rear view of the rotary solenoid of FIG. 1.

FIG. 3 shows a schematic plan view of the rear of the solenoid 40. The arrow indicates the movement of the lever 110 from one extreme of rotation to the other.

The purpose of the optical sensor is to determine the position of the crank system. At one extreme of rotation, the shutter 118 is received within the opening 112, and hence blocks the light from the optical source so that nothing is detected by the detector. At the opposite extreme of rotation, the shutter 118 is removed from the opening 112 so that light from the optical source is detected by the detector. Hence it is possible to determine from the state of the detector signal in which of the two extremes of rotation the crank system is located. In turn, this determines which polarity of pulse needs to next applied to the solenoid 40, to move the crank system to the other extreme of rotation. Therefore, the detector signal is fed to the solenoid power source to control the pulse polarity.

A crank system having a bottom dead center is a particularly advantageous way of configuring the positioning mechanism.

FIG. 4 shows a schematic diagram of the crank system in a number of positions, including bottom dead center. The second crank shaft 34 is shown in its two extreme positions (solid outline and broken outline), and also at a number of intermediate positions in which it is represented by solid lines for the sake of clarity. The first crank shaft 32 is represented by solid lines in all cases.

At the extreme left position of the second crank shaft (solid outline), the angle between the two crank shafts is at a minimum. The position of the lower end of the first crank shaft 32 is constrained by the linear bearing of the pin head 10 to lie on the vertical axis of movement of the pin holder 12. At this minimum angle, the pin holder is at its uppermost position. As the second crank shaft 34 moves away from the extreme left position, the angle between the crank shafts increases, and the lower end of the first crank shaft moves down the vertical axis, carrying the pin holder 12 with it. This continues until the angle between the crank shafts reaches a maximum of 180°, at which point the crank system is at bottom dead center, and extended to its maximum reach, so that the pin holder has been moved to the lowest position achievable. As the second crank shaft moves past the bottom dead center position towards its extreme right position (broken outline), the reverse process occurs until the pin holder is once again in the uppermost position.

An equivalent effect can be achieved by locating the crank system in some orientation other than that shown in FIGS. 1 and 4, so that, for example, the lowest position of the pin holder 12 corresponds to one or both of the extreme positions of the second crank shaft 34. More complex crank systems having more than two crank shafts may also be used. However, the use of the bottom dead center position to define the lowest position is to be preferred. It is to be understood throughout this application that the term bottom dead center refers also to the positions of other crank system orientations in which the lowest position is achieved.

FIG. 5 shows a graph of the variation of the vertical position x of the pin holder with time t, as the solenoid current is reversed. If the second crank shaft 34 was driven continuously around and around, the pin holder position would vary in a sinusoidal fashion as shown by line 100. However, as the second crank shaft 34 is constrained to travel over only 110°, and also because the solenoid is powered by the reversing of the current supply, the movement of the pin holder 12 is limited to that portion of the sine wave under the line 102. The pin holder moves between the uppermost position 104 and the lowest position 106.

It is noted that, as the pin holder 12 approaches the lowest position, the slope of the graph becomes less and less, reaching zero at the lowest position. This indicates that the velocity and acceleration of the pin holder also reduce and reach zero as it approaches the lowest position (assuming continuous rotation of the crank through the turning point at bottom dead center). Therefore, the chances of damage to the pins 20 or to slides or other parts of a microarraying apparatus owing to unexpected impact are reduced, and the quality of the spotting is enhanced since ample time will be allowed for a controlled release of the spotting liquid carried by the pin onto the spotting surface. Also, the pins 20 are retained in the pin holder 12 more securely. As mentioned, the pins 20 hang freely under their own weight in the pin holder 12, so that if the pin holder 12 moves downwards too quickly, the pins 20 can be left behind, and possibly not reach their lowest position before the pin holder 12 begins to move upwards again, collecting the pins 20 on the way. The low velocity and acceleration about the lowest position prevent this from occurring, so that the tips of the pins 20 reach their lowest position at the same time as the pin holder 12. This low velocity behavior is an advantageous feature of driving the pin head 12 with a rotational drive coupled to a crank system, which imparts the sinusoidal motion to the pin head 12.

Second Embodiment of Pin Head

As described above, the first embodiment uses a rotary solenoid as the vertical drive for the pin head. An alternative embodiment uses a rotary electric motor in place of the rotary solenoid. The structure and function of the pin head is otherwise identical to that of the first embodiment shown in FIG. 1, and the same reference numerals will be used to refer to corresponding parts. The rotary motor performs the same function as a rotary solenoid, in that the second crank shaft 34 is rotated so that the pin holder 12 reaches its lowest position when the crank system is at bottom dead center.

FIG. 6 shows a partly exploded perspective view of a pin head driven by a rotary motor. As before, the pin head 10 comprises a pin holder 12 for holding pins 20 which is mounted on one side of a vertical member 22 having a linear bearing at its upper end. A peg 30 on the reverse side of the vertical member 22 couples the pin head 10 to a crank system comprising a first crank shaft 32 and a second crank shaft 34. The second crank shaft is coupled to an axle 38 driven by a rotary stepper motor 126. The motor 126 is powered in the conventional manner.

In operation, the rotary motor rotates fully, so that the second crank shaft 34 performs complete revolutions. Once per revolution, the crank system therefore passes through its bottom dead center and its top dead center. The bottom dead center takes the pins in the pin holder to their lowest position, and the highest position of the pins occurs at top dead center. This is in contrast to the rotary solenoid embodiment described above, in which the second crank shaft moves back and forth over a fraction of a full revolution, so that the crank system never reaches bottom dead top. The crank system can be set to bottom dead center, and hence the pins set to their lowest position, by manual rotation of the motor until the position is reached.

FIG. 7 shows a schematic depiction of the rotation of the crank system. The first crank shaft 32 and the second crank shaft 34 are shown in an intermediate position which locates the pins between the highest and lowest positions. As the second crank shaft 34 is rotated by the motor 126, as shown by the arrow in FIG. 7, it carries the first crank shaft with it so that the crank system passes first through top dead center 128 and then through bottom dead center 130.

FIG. 8 shows a graph of the variation of the vertical position x of the pin holder with time t, as the motor rotates the crank system. The motion is sinusoidal, with a period T corresponding to one revolution. As before, for the rotary solenoid, the velocity of the pins is zero at the lowest position. The pins have maximum velocity at the position 134 intermediate between the lowest position 132 and the highest position 136.

Pin Head Height Adjustment Mechanism

Figure 9:
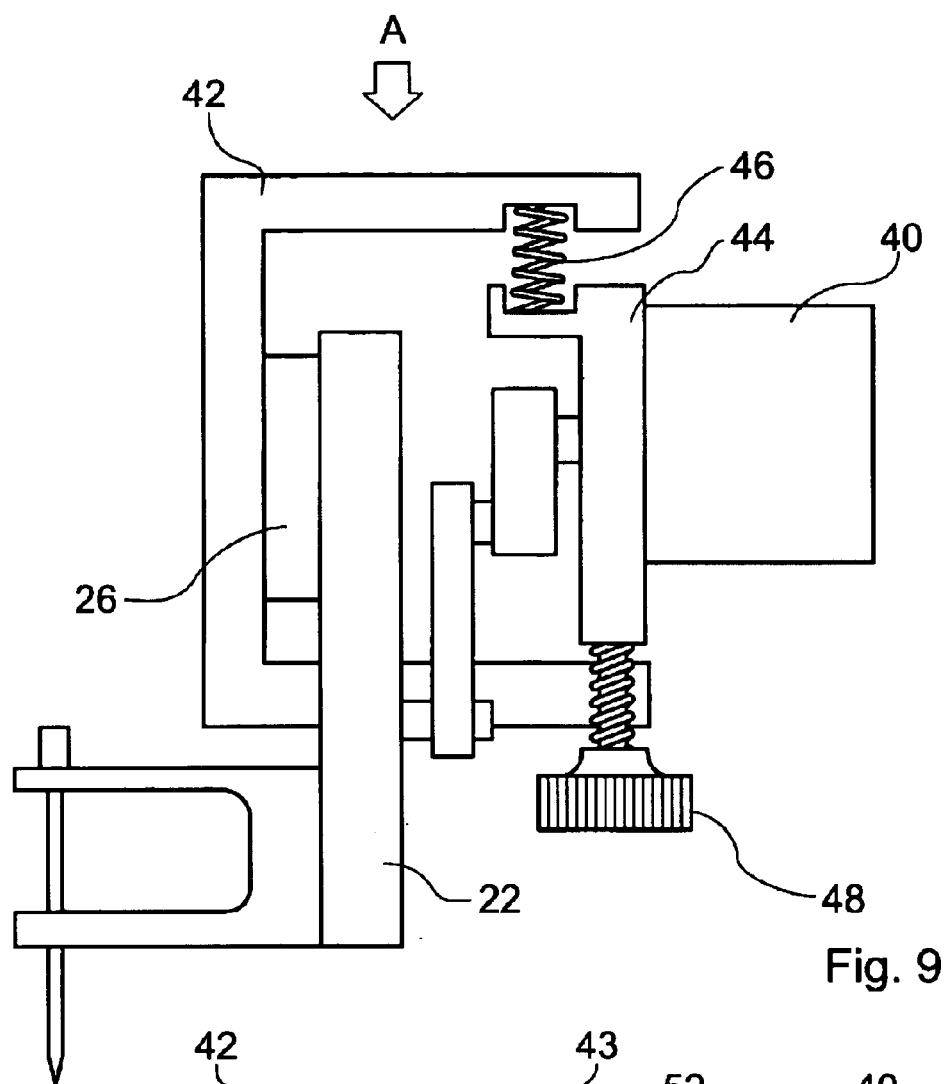
FIG. 9 shows a cross-sectional side view of part of a pin head with integral height adjustment.

FIG. 9 shows a cross-sectional side view of a pin head provided with a vertical height adjustment arrangement. The pin head may be according to any of the embodiments described above.

The vertical member 22 is attached to the attachment member 26 by means of the linear bearing in the manner previously described. The attachment member 26 is fixed on the inside of a C-shaped (in vertical cross-section) mount 42. The mount 42 is used to fasten the pin head 10 to a microarraying apparatus.

The pin head 10 is held within the mount 42 by an adjustment member 44. The adjustment member is fixed to the solenoid 40 (or motor 126), and is held vertically within the mount by a biasing spring 46 and an adjusting screw 48. The adjusting screw 48 screws upwards through a threaded hole in the mount 42, and passes through the mount 42 so as to abut the underside of the adjustment member 44. The adjustment member 44 is supported on the adjusting screw 48. The biasing spring 46 extends between the upper side of the adjustment member 44 and the underside of the upper arm of the mount 42 so as to bias the adjustment member 44 and the mount 42 apart.

To adjust the height of the pin head 10, the adjusting screw 48 is turned so as to move further into or out of the threaded hole. Because the adjustment member 44 rests on the screw 48, the adjustment member moves up or down accordingly, and is held in contact with the adjusting screw 48 by the biasing spring 46. The spring 46 thus ensures that the adjustment member follows the movement of the screw.

The adjustment member 44 is attached to the solenoid 40, which is in turn coupled to the vertical member 22 by the crank shafts, so that as the adjustment member moves, the vertical member 22 slides up or down along the linear bearing. The vertical member 22 hence moves relative to the mount 42. Therefore the height of the pin head relative to the mount 42 can be altered by turning the adjusting screw 48. The mount 42 attaches the pin head 10 to a microarraying apparatus, so this has the effect of altering the lowest position which the pins can reach relative to the surface of the apparatus. A scale can be provided so that heights can be recorded and replicated.

Figure 10:
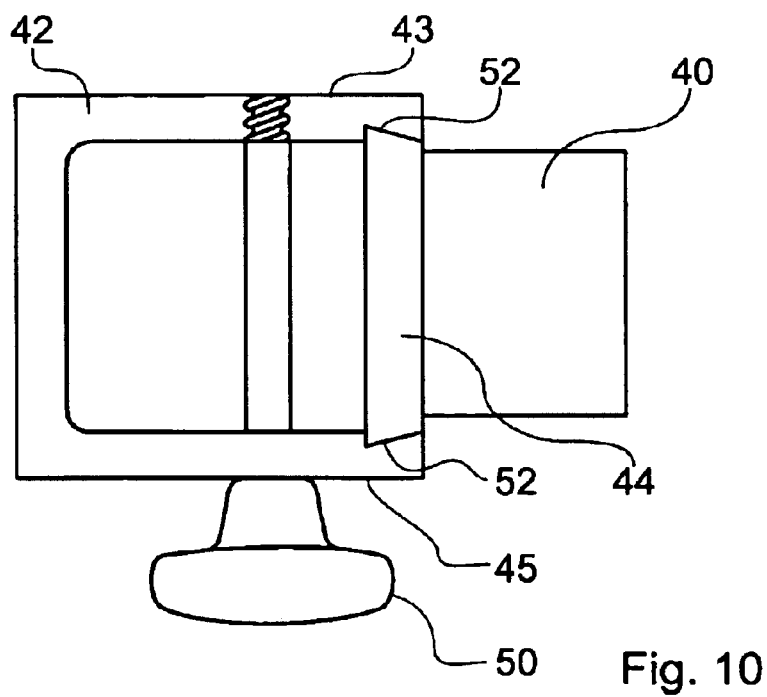
FIG. 10 shows a cross-section top view of the pin head of FIG. 9.

FIG. 10 shows a further cross-sectional view of the pin head, along the direction 'A' in FIG. 9. The mount 42 is C-shaped in horizontal cross-section. A locking screw 50 passes through a hole in one side 45 of the mount 42 and is screwed into a threaded hole on the opposite side 43 of the mount 42. Tightening of the locking screw 50 pulls the two sides 43, 45 of the mount 42 towards one another.

Each side of the mount 42 is provided with a vertical channel 52, which receive the adjustment member 44 with the solenoid 40 attached. As the locking screw 50 is tightened, the two sides 43, 45 of the mount 42 clamp the adjustment member 44 between them.

This feature allows the pin head 10 to be more firmly secured to the mount 42. When the height of the pin head 42 is to be adjusted, the locking screw 50 is loosened so that the adjustment member 44 can slide within the channels 52, and hence move up or down as the adjusting screw 48 is turned. After the height is set, the locking screw 50 is tightened to hold the pin head 10 firmly in position.

The purpose of this feature of vertical adjustment is to permit a user to manually and readily alter the lowest pin position achieved by the pin holder with respect to the microarraying apparatus, so that the lowest pin position can be set to coincide with a pin position which needs to be repeatedly achieved, such as contacting the surface of slides with the pins for spotting in a microarraying process.

Although similar adjustment can be achieved by moving both the apparatus bed and well plate platform together in the vertical direction, the provision of a mechanism on the pin head for adjusting the bottom pin position is more convenient, since it avoids having to move two or more components together (the apparatus bed, well plate platform and any other platform). In addition, with this approach, there is no need to provide a mechanism for adjusting the height of the surface supporting the microscope slides. In other words, the apparatus bed can be a simple non-adjustable block.

Microarrayer

Figure 11:
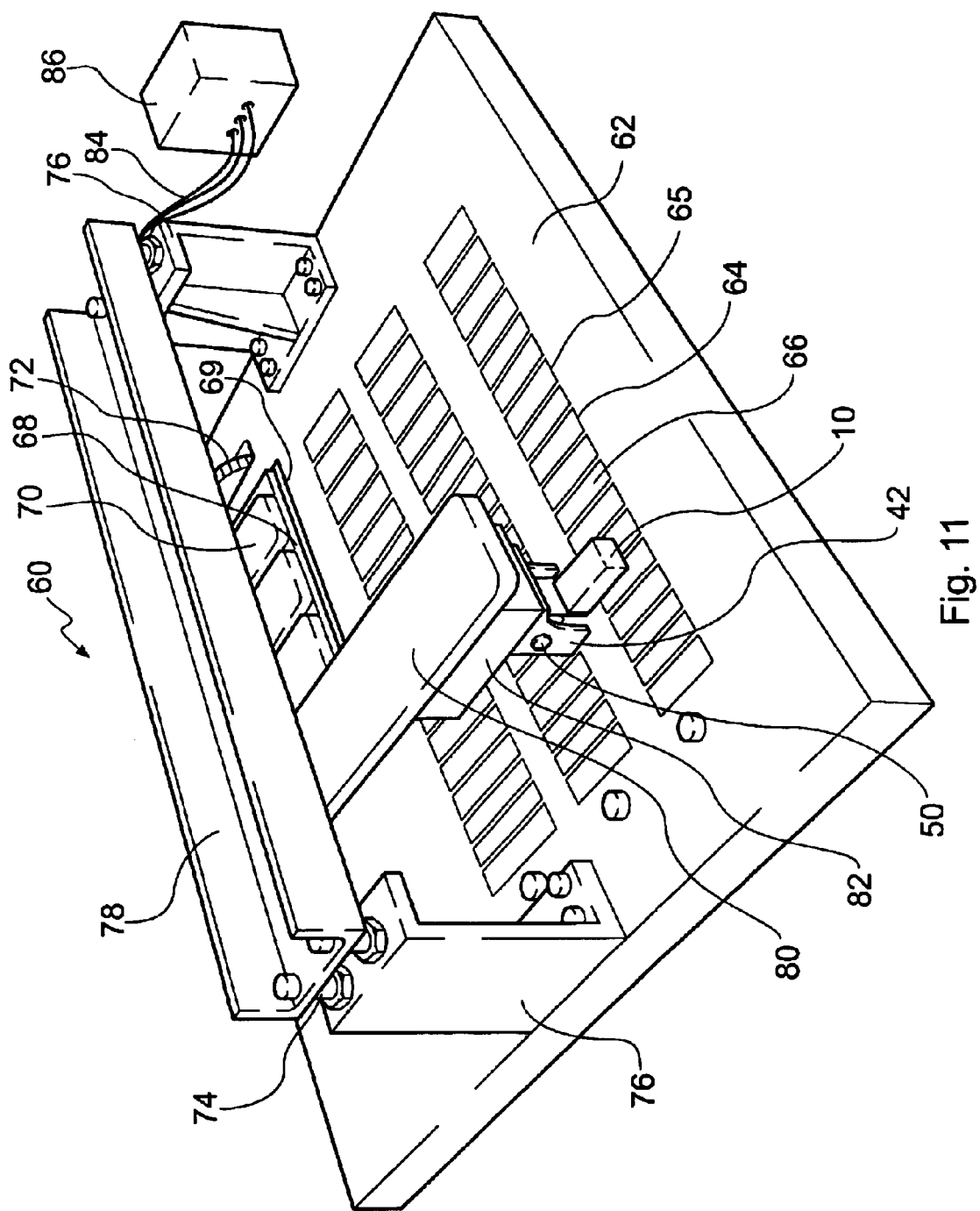
FIG. 11 shows a perspective view of a microarraying apparatus embodying the invention.

FIG. 11 shows a perspective view of a microarraying apparatus 60 according to an embodiment of the invention, which may include a pin head according to any of the above described designs. The apparatus 60 comprises a microarraying surface 62, constituted by the main bed of the apparatus. The surface 62 may optionally have in it a plurality of shallow depressions 64, each of which has dimensions slightly larger than a standard microscope slide. The depressions 64 together form a slide holder or locator 65, and each depression 64 receives a slide 66.

The surface 62 also has a well plate platform 68, which has a number of shallow depressions each large enough to receive and locate a well plate 70. The well plate platform 68 is not integral with the surface 62. Instead, it is a separate planar member which fits within an aperture 69 in the surface 62. Underneath the well plate platform 68 is an elevating mechanism, for example a jack, operable to raise and lower the well plate platform 68 with respect to the surface 62. The elevating mechanism is operated by means of a dial 72 protruding from the surface 62. Turning the dial 72 in one direction raises the well plate platform 68, and turning it in the opposite direction lowers the well plate platform 68. The dial 72 has a scale marked on it indicating the amount by which the well plate platform 68 is raised or lowered. The scale also indicates when the well plate platform 68 is in a position in which the top of well plates 70 in the well plate platform 68 are level with the top of slides 66 in the slide holder 65.

In this embodiment the elevating mechanism is purely mechanical for simplicity of construction, low cost and ease of use. However, in other embodiments any other known elevating mechanism could be used, for example using an electric motor.

A frame 74 is mounted over the surface 62. The frame 74 comprises two elongate uprights 76 affixed at their lower ends to the surface 62, and a cross-bar 78 joining the upper ends of the uprights 76. A horizontal arm 80 is mounted on a track on the underside of the cross-bar 78.

The arm 80 has on its underside a further track, mounted on which is a pin head 10. The pin head 10 can be according to any of the embodiments described above; however, for the purposes of example only, the following description assumes a pin head 10 having a rotary solenoid and a crank system according to the first embodiment. A mount 42 having a height adjustment mechanism with a locking screw 50 couples the pin head 10 to the track. A housing 82 houses the vertical drive of the pin head 10.

The frame 74 is motorized to provide movement of the pin head 10 in a plane parallel to the surface 62. Control wires 84 to control and power the motorization pass along the underside of the arm 80 and the cross-bar 78 to a power supply and control box 86. Further wires 84 connecting the vertical drive to the power supply are also provided. The pin head 10 can travel along the length of the arm 80, riding on the track, and the arm 80 in turn can travel along the length of cross-bar 78, also by riding on the track. Thus the pin head can move to a position above any slide 66 in the slide holder 65, and any well plate 70 in the well plate platform 68. Vertical movement of the pin head, towards and away from the surface 62, is provided by the vertical drive.

To operate the microarraying apparatus, a slide 66 of the same thickness as slides to be spotted by the microarraying apparatus is placed into the slide holder. The pin head 10, having pins in its pin holder, is moved to a position above the slide. No current is supplied to the solenoid, so the pins in the pin holder are in their lowest position. Using the head 46 of the adjustment screw on the mount 42, the pin head 10 is lowered manually until the pins are in the position needed to spot the slide (for example, the tips of the pins just contact the slide surface, or are just above it, depending on the spotting technique to be applied). Application of current to the solenoid then moves the pin holder to its upper position, well clear of the slide surface.

Next, the height of the well plate platform 68 is adjusted, using the dial 72. The height is first set to that at which the tops of well plates are level with the tops of slides, as this means that the lowest pin position will be such that the tips of the pins are approximately level with the top of the well plate. Given the depth of the wells in the well plates, the depth of fluid in the wells and the depth to which the pins need to dip into the fluid, the height of the well plate platform 68 is adjusted until the lowest pin position coincides with the pin position required to dip the pins into the wells.

Once the positions of the pin head 10 and the well plate platform have been set, well plates 70 are placed into the well plate platform 68 and slides 66 are placed into the slide holder 65, and the microarraying procedure can be carried out. Movement of the pin head 10 over the surface 62 by control of the motorized frame 74 is carried out in the conventional way. Current is applied to the solenoid while the pin head 10 is travelling over the surface, to keep the pin holder in its upper position so that the pins are clear of the slides and well plates. However, each time the pins are required to dip into the wells or spot the slides, the current applied to the solenoid is reversed so that the pin holder moves from its upper position to its lowest position (where spotting or dipping occurs) and back to its upper position for further travel over the surface.

The microarraying apparatus depicted in FIG. 11 is of a small size, for the handling of modest quantities of well plates and slides. This small size makes the apparatus portable, and well-suited for use in situations where microarraying is carried out on a small or infrequent scale.

Figure 12:
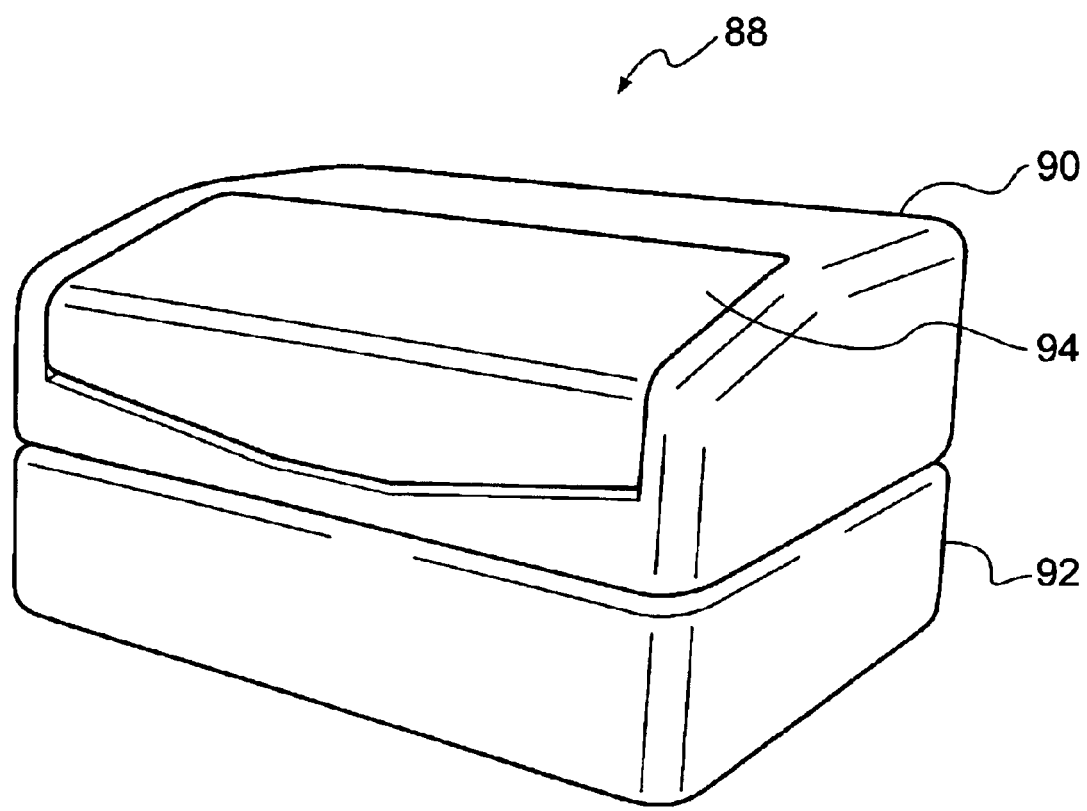
FIG. 12 shows a perspective view of the microarraying apparatus of FIG. 11 when housed.

FIG. 12 shows a perspective view of a housing 88 for encasing the microarraying apparatus 60. The housing 88 comprises an upper part 90 and a lower part 92 which in use, when encasing an apparatus, are sealed together. However, the two parts 90, 92 can be taken apart to allow the apparatus to be removed from the housing 88, for maintenance, repair and the like. The upper part 90 has an openable transparent window 94. Operation of the apparatus can be observed through the window, and it can be opened to give access to the apparatus.

Alternative Embodiments

Constructions alternative to that of FIGS. 9 and 10 may be used to provide the manual adjustment offered by the pin head mount. For example, a gearing system may be incorporated into the screw thread adjustment to allow finer control and more accurate control of the position of the pin holder.

Although the main embodiment describes a spotting surface without height adjustment in combination with a height adjustable well plate platform, it will be appreciated that the spotting surface may be height adjustable and the well plate non-height adjustable. Alternatively, both the well plate platform and spotting surface may be provided with height adjustment facilities. All that is required is that they be relatively adjustable by known amounts so that they can be set into the correct positions for spotting and dipping once the lowest pin holder position has been set to coincide with one of these positions. Indeed, if adjustment to both the slide holder and the well plate platform is provided, it is possible to dispense with the manual adjustment of the pin head. The slide holder and well plate platform can be locked together at the same height, and moved together so that the slide is in the spotting position under the pins in their lowest position. The holders can then be unlocked, and the well plate platform adjusted to provide the necessary height difference from the slide holder.

A variety of interchangeable well plate platforms can be provided, each accommodating different sizes of well plate, as these are commonly available in a number of sizes having varying numbers of wells.

It will also be understood that references to slides or microscope slides for providing the spotting surface are made for clarity. Of course, a wide variety of items may be used to provide a spotting surface, some of which may not normally be termed as slides in the art. The term slide as used in this document should be construed as meaning any item that provides a spotting surface.

The bottom position of the pins may preferably be defined by a de-energized or off state of an electrical actuation signal to the vertical drive for the pins, as described above for the rotary solenoid embodiment. Alternatively, the bottom position may be defined by an energized or on-state of the electrical actuation signal. Moreover, although the above-described simple two-state electrical actuation signal is preferred, a more complex multi-state or analog electrical actuation signal could be used.

Instead of a crank-based rotary drive, in another embodiment, a linear motor may be used to drive the pin head vertically, in combination with a positioning mechanism comprising an abutment against which the pin holder or vertical member abuts. The abutted position defines the lowest position of the pins.

It will be appreciated that although particular embodiments of the invention have been described, many modifications/additions and/or substitutions may be made within the spirit and scope of the present invention.

What is claimed is:

1. A microarraying apparatus comprising:
   an apparatus bed defining an arraying surface for carrying one or more slides providing a spotting surface;
   a well plate platform for carrying at least one well plate;
   a pin head accommodating an array of pins that have a mechanically defined lowest point of travel; and
   a height adjustment mechanism operable to alter the height of the well plate platform relative to that of the apparatus bed, to pre-align the relative heights of the spotting surface and the well plates such that pins in the pin head can be lowered to the mechanically defined lowest point of travel both for picking up liquid from the well plate and for depositing liquid onto the spotting surface.

2. A microarraying apparatus, comprising:
   an apparatus bed defining an arraying surface for carrying one or more slides;
   a well plate platform for carrying at least one well plate; and
   a manually actuatable height adjustment mechanism operable to alter the height of the well plate platform relative to that of the apparatus bed.

3. A microarraying apparatus according to claim 2, in which the height adjuster is provided with a distance scale indicative of the height of the well plate platform relative to that of the apparatus bed.

4. A microarraying apparatus comprising:
   an apparatus bed defining an arraying surface for carrying one or more slides;
   a well plate platform for carrying at least one well plate;
   a height adjustment mechanism operable to alter the height of the well plate platform relative to that of the apparatus bed;
   a mounting frame mounted over the apparatus bed; and
   a pin head mounted on the mounting frame and being provided with a drive system operable to move the pin head across the arraying surface, the pin head comprising a pin holder for holding an array of pins, a vertical drive operable to move the pin holder in a vertical axis transverse to the arraying surface, and a positioning mechanism that mechanically defines a bottom position of the pin holder.

5. A microarraying apparatus according to claim 4, further comprising a height adjustment arrangement manually operable to adjust the bottom position by adjusting a vertical distance between the mounting frame and the pin head.

6. A microarraying apparatus according to claim 4, in which the positioning mechanism comprises a crank system having a bottom dead center and coupled to the pin holder so that the pin holder achieves its lowest position when the crank system is at bottom dead center.

7. A microarraying apparatus according to claim 6, in which the vertical drive comprises a rotary solenoid which is coupled to the pin holder by the crank system, the crank system operable to transfer motion produced by the rotary solenoid to the pin holder.

8. A microarraying apparatus according to claim 6, in which the vertical drive comprises a rotary motor which is coupled to the pin holder by the crank system, the crank system operable to transfer motion produced by the rotary motor to the pin holder.

9. A microarraying apparatus according to claim 4, wherein said height adjustment mechanism is manually actuatable.

10. A spotting method using the microarraying apparatus of claim 2, the method comprising:
    arranging at least one slide on the apparatus bed to provide a spotting surface;
    arranging a well plate filled to a level with spotting liquid on the well plate platform;
    vertically aligning the well plate platform relative to the apparatus bed by manually actuating the height adjustment mechanism so that the spotting surface lies at a desired height at or below the level of the spotting liquid;
    dipping one of the pins from the pin head into the spotting liquid by moving the pin to a lowered position;
    moving the pin head across the microarraying apparatus to a spotting position; and
    depositing the spotting liquid onto the spotting surface by moving the pin once again to the lowered position.

11. A spotting method using the microarraying apparatus of claim 4, the method comprising:
    arranging at least one slide on the apparatus bed to provide a spotting surface;
    arranging a well plate filled to a level with spotting liquid on the well plate platform;
    vertically aligning the well plate platform relative to the apparatus bed so that the spotting surface lies at a desired height at or below the level of the spotting liquid;
    dipping one of the pins from the pin head into the spotting liquid by moving the pin to a lowered position defined by the bottom position of the pin holder;
    moving the pin head across the microarraying apparatus to a spotting position; and
    depositing the spotting liquid onto the spotting surface by moving the pin once again to the lowered position.

12. A spotting method using a microarraying apparatus having an apparatus bed, a pin head holding a plurality of pins, and a well plate platform, the method comprising:
    arranging at least one slide on the apparatus bed to provide a spotting surface;
    arranging a well plate filled to a level with spotting liquid on the well plate platform;
    vertically aligning the well plate platform relative to the apparatus bed so that the spotting surface lies at a desired height at or below the level of the spotting liquid;
    dipping one of the pins from the pin head into the spotting liquid by moving the pin to a lowered position;
    moving the pin head across the microarraying apparatus to a spotting position; and
    depositing the spotting liquid onto the spotting surface by moving the pin once again to the lowered position.

13. The method of claim 12, wherein the vertical aligning step is performed by manual actuation of a height adjustment mechanism operable to alter the height of the well plate platform relative to that of the apparatus bed.

14. The method of claim 12, wherein the pin head has a mechanically defined bottom position.

* * * * *